United States Patent [19]

Schaaf et al.

[11] 4,065,472
[45] Dec. 27, 1977

[54] 5-(2-CARBOXYTHIOPHEN-5-YL)-16-ARYLOXY-α-TETRANOR-ω-TETRANOR-PROSTAGLANDINS

[75] Inventors: Thomas K. Schaaf, Old Lyme; Jasjit Singh Bindra, Groton, both of Conn.

[73] Assignee: Pfizer Inc., New York, N.Y.

[21] Appl. No.: 617,481

[22] Filed: Sept. 29, 1975

[51] Int. Cl.$^2$ ............... C07D 333/24; A01N 9/00
[52] U.S. Cl. ............... 260/332.2 C; 260/332.3 R; 260/332.5; 424/275
[58] Field of Search ............... 260/332.2 C

[56] References Cited

U.S. PATENT DOCUMENTS 3,922,289    11/1975    Patterson et al. ............... 260/332.2

FOREIGN PATENT DOCUMENTS 1,350,971    4/1974    United Kingdom.

*Primary Examiner*—Bernard Helfin
*Assistant Examiner*—A. Siegel
*Attorney, Agent, or Firm*—Connolly and Hutz

[57] ABSTRACT

5-(2-Carboxythiophen-5-yl)-16-aryloxy-α-tetranor-ω-tetranorprostaglandins and intermediates useful in their preparation are disclosed. The novel prostaglandins of this invention have been found to have activity profiles comparable to the parent prostaglandins but they exhibit a greater tissue specificity of action.

7 Claims, No Drawings

5-(2-CARBOXYTHIOPHEN-5-YL)-16-ARYLOXY-α-TETRANOR-ω-TETRANORPROSTAGLANDINS

BACKGROUND OF THE INVENTION

This invention relates to certain novel analogs of the naturally occurring prostaglandins. In particular, it relates to novel 5-(2-carboxythiophen-5-yl)-16-aryloxy-α-tetranor-ω-tetranorprostaglandins and various novel intermediates useful in their preparation.

The prostaglandins are C-20 unsaturated fatty acids which exhibit diverse physiological effects. Each of the known, naturally occurring prostaglandins is derived from prostanoic acid which has the structure and position numbering:

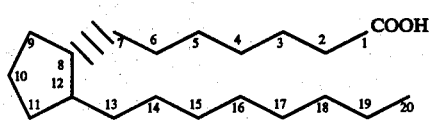

[Bergstrom et al., Pharmacol. Rev. 20, 1 (1968), and references cited therein.] A systematic name for prostanoic acid is 7-[(2β-octyl)-cyclopent-1α-yl]heptanoic acid.

PGA$_2$ has the structure:

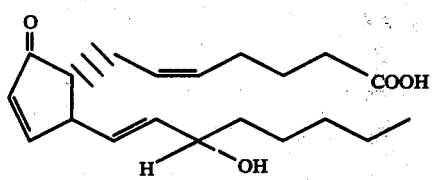

PGB$_2$ has the structure:

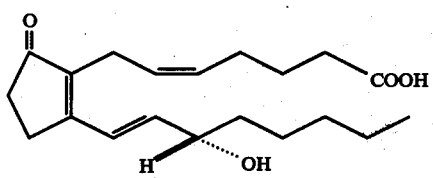

PGE$_2$ has the structure:

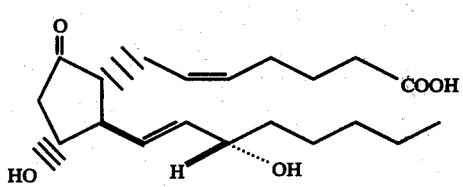

PGF$_{2\alpha}$ has the structure:

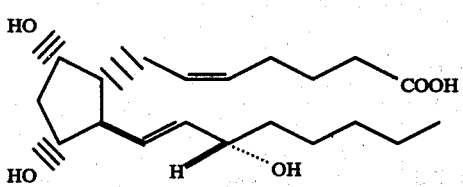

PGF$_{2\beta}$ has the structure:

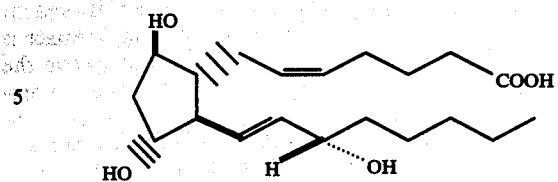

Each of the PG$_1$ prostaglandins, PGE$_1$, PGF$_{1\alpha}$, PGF$_{1\beta}$, PGA$_1$, and PGB$_1$, has a structure the same as the corresponding PG$_2$ compound except that the cis double bond between C-5 and C-6 is replaced by a single bond. For example, PGA$_1$ has the structure:

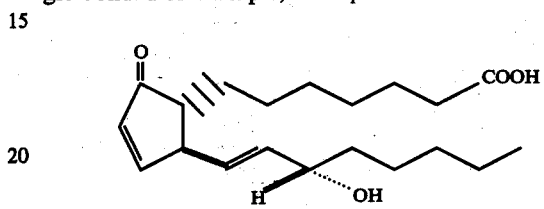

The PG$_0$ compounds are those in which there are no double bonds in either side chain. For instance, PGE$_0$ has the structure

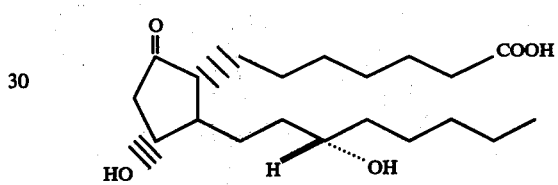

Broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

The side-chain hydroxy at C-15 in the above formulas is in S configuration. [See, Nature, 212, 38 (1966) for discussion of the stereochemistry of the prostaglandins.]

Molecules of the known prostaglandins each have several centers of asymmetry, and can exist in racemic (optically inactive) form and in either of the two enantiomeric (optically active) forms, i.e., the dextrorotatory and levorotatory forms. As drawn above, each structure represents the particular optically active form of the prostaglandin which is obtained from certain mammalian tissues, for example, sheep vesicular glands, swine lung, or human seminal plasma, or by carbonyl and/or double bond reduction of that prostaglandin. [Bergstrom et al., cited above.] The mirror image or optical antipode of each of the above structures represents the other enantiomer of that prostaglandin. For instance, the optical antipode of PGF$_{2\alpha}$ (ent-PGF$_{2\alpha}$) is drawn as

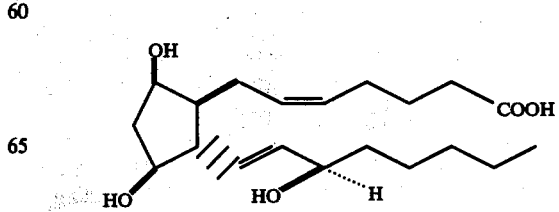

The racemic form of a prostaglandin contains equal numbers of a particular stereoisomer and its mirror image. When reference to a prostaglandin racemate is intended, the symbols "rac" or "dl" will precede the prostaglandin name. Two structures are needed to represent a racemate. For instance, the structure of dl-PGF$_{2\alpha}$ is properly represented as an equimolar mixture of PGF$_{2\alpha}$ and ent-PGF$_{2\alpha}$. The terms PGE$_1$, PGE$_2$, PGF$_{1\alpha}$ and the like as used herein will mean that stereoisomer with the same absolute configuration as the corresponding prostaglandin found in mammalian tissue.

In an optical antipode, the absolute configuration at all of the above-mentioned centers of asymmetry is inverted. In an epimer, the configuration is inverted at one or more but not all of the centers. For instance, the absolute configuration of the 15-hydroxy group in 15-epi-PGF$_{2\alpha}$ is the R configuration and is shown as

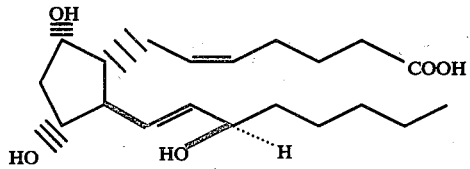

It will be noted that only the configuration at the 15-position is inverted and that at the other centers of asymmetry, namely the 8-, 9-, 11- and 12-positions, the absolute configuration is the same as that in the naturally-occurring mammalian PGF$_{2\alpha}$. Mixtures of epimers may also exist for instance, if 15-keto-PGF$_{2\alpha}$ is reduced with zinc borohydride or a hindered alkyl borohydride, the resulting product is a racemic mixture of 15α-hydroxy and 15β-hydroxy-PGF$_{2\alpha}$.

PGE$_1$, PGE$_2$, and the corresponding PGF$_\alpha$, PGF$_\beta$, PGA, and PGB compounds, and many of their derivatives such as the esters, acylates and pharmacologically acceptable salts, are extremely potent inducers of various biological responses. These compounds are, therefore, potentially useful for pharmacological purposes. [Bergstom et al., cited above.] A few of those biological responses are systemic arterial blood pressure lowering in the case of the PGF$_\beta$, PGE and PGA compounds as shown in cardiac cannulated rats or dogs; pressor activity for the PGF$_\alpha$ compounds; stimulation of smooth muscle as shown by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury; in the case of the PGE and PGB compounds, stimulation of epidermal proliferation and keratinization as shown when applied in culture to embryonic chick and rat skin segments; and in the case of PGF$_2$ and PGE compounds luteolytic activity as shown in hamsters and rats.

Prostaglandins are useful to prevent, control, or alleviate a wide variety of diseases and undesirable physiological conditions in avians and mammals, including humans, useful domestic animals, pets, and zoological specimens, and in laboratory animals, for example, mice, rats, rabbits, and monkeys.

For example, these compounds, especially those of the E series, are useful in mammals, including man, as bronchodilators [Cuthbert, Brit. Med. J., 4: 723–726, 1969]. As nasal decongestants, the compounds are used in a dose range of about 10 μg. to about 10 mg. per ml. of a pharmacologically suitable liquid vehicle or as an aerosol spray, both for topical application.

The PGE compounds are useful in the treatment of asthma because of their activity as bronchodilators and/or as inhibitors or mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of routes in a number of dosage forms, e.g., orally in the form of tablets, capsules, or liquids; rectally in the form of suppositories; parenterally with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day. These prostaglandins can also be combined advantageously with other anti-asthmatic agents, such as sympathomimetics (isoproterenol, phenylephrine, ephedrine, etc.); xanthine derivatives (theophylline and aminophyllin); and corticosteroids (ACTH and prednisolone). Regarding use of these compounds see South African Pat. No. 68/1055.

The PGE and PGA compounds are useful in mammals, including man and animals to reduce and control excessive gastric secretion, thereby reducing or avoiding gastrointestinal ulcer formation, and accelerating the healing of such ulcers already present in the gastrointestinal tract. [Shaw and Ramwell, In: Worchester Symposium on Prostaglandins, Wiley (New York, 1968), pp. 55–64.] For this purpose, the compounds are administered parenterally by injection or intravenous infusion in an infusion dose range of about 0.1 μg. to about 500 μg. per kg. of body weight per minute, or in a total daily dose by injection or infusion in the range of about 0.1 to about 20 mg. per kg. of body weight per day.

The PGE compounds are useful whenever it is desired to inhibit platelet aggregation, to reduce the adhesive character of platelets, and to remove or prevent the formation of thrombi in mammals, including man, rabbits, and rats. [Emmons et al., Brit. Med. J., 2: 468–472, 1967.] These compounds are, for example, useful in the treatment and prevention of mycardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically. For rapid response, especially in emergency situation, the intravenous route of administration is preferred. Doses in the range of about 0.005 to about 20 mg. per kg. of body weight per day are used.

The PGE compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to the new body. Under such conditions, aggregated platelets tend to block the blood vessels and portions of the circulation apparatus. Such aggregation is inhibited by the presence of a prostaglandin. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter or circulating fluid.

PGE and $PGF_\alpha$ compounds are extremely potent in causing stimulation of smooth muscle, and are also highly active in potentiating other known smooth muscle stimulators. Therefore, $PGE_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered intravenously immediately after abortion or delivery at a dose in the range of about 0.01 to about 50 µg. per kg. of body weight per minute until the desired effect is obtained. Subsequent doses are given parenterally during puerperium in the range 0.01 to 2 mg. per kg. of body weight per day.

The PGE, PGA and $PGF_\beta$ compounds are useful as hypotensive agents and vasodilators [Bergstrom et al., Acta. Physiol. Scand., 64: 332–333, 1965; Life Sci., 6:449–455, 1967] in mammals, including man. To lower systemic arterial blood pressure, the compounds are administered by intravenous infusion at the rate of about 0.01 to about 50 µg. per kg. of body weight per minute, or in single or multiple doses of about 25 to 500 µg. per kg. of body weight total per day. [Weeks and King, Federation Proc. 23:327, 1964; Bergstrum, et al., 1965, op. cit.; Carlson, et al., Acta Med. Scand. 183:423–430, 1968; and Carlson et al., Acta Physiol. Scand. 75:161–169, 1969.]

The PGA and PGE compounds and derivatives and salts thereof increase the flow of blood in the mammalian kidney, thereby increasing volume and electrolyte content of the urine. For that reason, the compounds are useful in managing cases of renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephretic states, the vasopressin action of these compounds is especially useful. Illustratively, the compounds are useful in alleviating and correcting cases of edema resulting from massive surface burns, in the management of shock, etc. For these purposes, the compounds are preferably first administered by intravenous injection at a dose in the range 10 to 1000 µg. per kg. of body weight or by intravenous infusion at a dose in the range 0.1 to 20 µg. per kg. of body weight per minute until the desired effect is obtained. Subsequent doses are given by intravenous, intramuscular, or subcutaneous injection or infusion in the range 0.05 to 2 mg. per kg. of body weight per day.

The PGE compounds, especially $PGE_1$, are useful in the treatment of psoriasis (Ziboh, et. al., Nature, 254, 351 (1975)). For this purpose, the compound is administered topically at a dose of 1–500 µg. 1 to 4 times daily until the desired effect is obtained.

The PGE, especially $PGE_2$, $PGF_\alpha$, and $PGF_\beta$ compounds are useful in the induction of labor in pregnant female animals, including man, cows, sheep, and pigs, at or near term [Karim et at., J. Obstet. Gynaec. Brit. Cwlth., 77:200–210, 1970] or in the induction of therapeutic abortion [Bygdeman et al., Contraception, 4, 293 (1971)]. For this purpose, the compound is infused intravenously at a dose of 0.01 to 50 µg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. Alternative routes of administration are oral, extraammiotic or intraammiotic.

The PGE, $PGF_\alpha$, and $PGF_\beta$ compounds are useful for fertility control in female mammals [Karim, Contraception, 3, 173 (1971)] including humans and animals such as monkeys, rats, rabbits, dogs, cattle, and the like. By the term ovulating female mammals is meant animals which are mature enough to ovulate but not so old that regular ovulation has ceased. For that purpose, $PFG_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

Patents have been obtained for several prostaglandins of the E and F series ad inducers of labor in mammals (Belgian Patent No. 754,158 and West German Patent No. 2,034,641), and one $PGE_1$, $E_2$ and $E_3$ for control of the reproductive cycle (South African Patent No. 69/6089). It has been shown that luteolysis can take place as a result of administration of $PGF_{2\alpha}$ [Labhsetwar, Nature, 230, 528 (1971)] and hence prostaglandins have utility for fertility control by a process in which smooth muscle stimulation is not necessary.

The PGE and $PGF_\alpha$ compounds are useful as antiarrhythmic agents (Forster, et. al., Prostaglandins, 3, 895 (1973)). For this purpose the compound is infused intravenously at a dose range of 0.5–500 µg/kg/minute until the desired effect is obtained.

As mentioned above, the PGE compounds are potent antagonists of epinephrine-induced mobilization of free fatty acids. For this reason, these compounds are useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGE and PGB compounds promote and accelerate the growth of epidermal cells and keratin in animals, including humans, useful domestic animals, pets, zoological specimens, and laboratory animals. For that reason, these compounds are useful in promoting healing of skin which has been damaged, for example, by burns, wounds, and abrasions, surgery, etc. These compounds are also useful in promoting adherence and growth of skin autografts, especially small, deep (Davis) grafts which are intended to cover skinless areas by subsequent outward growth rather than initially, and to retard rejection of homografts.

To promote the growth of epidermal cells, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, such as when there is substantial fluid loss as in the case of extensive burns or skin loss due to other causes, systemic administration is advantageous. Expecially in topical applications, these prostaglandins may be advantageously combined with antibiotics such as gentamycin, neomycin, polymyxin B, bacitracin, spectinomycin, tetracycline and oxytetracycline; with other antibacterials such as mafenide hydrochloride, sulfadiazine, furazolium chloride, and nitrofurazone; and with corticosteroids such as hydrocortisone, prednisolone, methylprednisolone, and fluprednisolone, each being used in the combination at the usual concentration suitable for its use alone.

In the preparation of synthetic pharmaceutical agents, among the principal objects is the development of analogs of naturally occurring compounds which are highly selective in their physiological activity and which have an increased duration of activity. In a series of compounds like the naturally-occurring prostaglandins which has an extremely broad activity spectrum, increasing the selectivity of a single compound usually involves the enhancement of one physiological effect and the diminution of the others. By increasing the selectivity, one would, in the case of the natural prostaglandins, expect to alleviate the severe side effects, particularly the gastrointestinal one frequently observed following systemic administration of the natural prostaglandins.

In order to achieve increased selectivity and duration of action in the prostaglandin series, many researchers have concentrated on the molecular modification of the last five carbons of the methyl-terminated side chain. One modification consists of removing one to four carbon atoms from the end of the lower side chain and terminating the chain with an aryloxy or heteroaryloxy group. Compounds of this type are described, for instance, in British Patent No. 1,350,971, the published Dutch Patent Application No. 73/06462 and Belgian Patent No. 806,995.

The 11-desoxy analogs of the natural prostaglandins have also been described, for instance, in the published Dutch patent publication No. 16,804, Belgian Patent No. 766,521 and the West German Offenlegungsschrift No. 2,103,005.

The analogs described below have been found to be more potent, longer acting, and more selective and possess unanticipated activities when compared to the natural prostaglandins or their 11-desoxy congeners. The present state of the art of knowledge about structure-activity correlations in the prostaglandins does not, however, permit one to explain the observed enhancement of selectivity in the compounds described below.

The particularly novel aspect of the compounds of the present invention is the termination of the top side chain with a carboxythiophene group. Though other modifications of the top side chain are known, they are by no means as common as modifications of the lower side chain. Belgian Patent No. 816,566 shows 11-desoxy prostaglandins with a 2,5-furylene, phenylene or oxaphenylene group next to the carboxy group in the top side chain; no modification of the lower side chain is shown. The West German Offenlegungsschrift No. 2,209,990 based in U.S. Ser. No. 121,572, filed Mar. 5, 1971 shows, among other things, an oxaphenylene group or an oxygen atom and a phenylene group separated by at least one methylene group in the top side chain; in some instances, the 15-position is substituted with a phenylalkyl group in which the alkyl chain may have from one to ten carbon atoms.

SUMMARY OF THE INVENTION

There is disclosed herein optically active compounds of the structure:

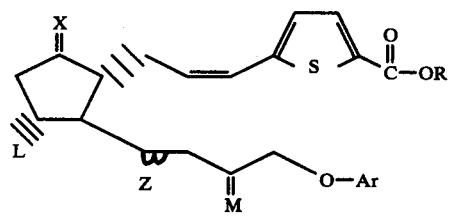

Their optical antipodes and their racemic mixtures in which there is a cis double bond at the 5-position and Z is a trans double bond or a single bond.

M and X are selected from the group consisting of keto,

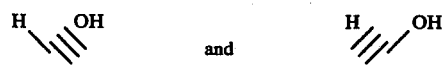

L is selected from the group consisting of hydrogen and hydroxyl.

R is selected from the group consisting of hydrogen, alkyl of from one to ten carbon atoms, cycloalkyl of from three to eight carbon atoms, phenyl, phenylalkyl of from seven to nine carbon atoms and mono-substituted phenyl wherein the substituent is selected from the group consisting of fluoro, chloro, bromo, iodo, alkyl and alkoxy of from one to six carbon atoms, and phenyl.

Ar is selected from the group consisting of phenyl, α-naphthyl, β-naphthyl and monosubstituted phenyl wherein the substituent is selected from the group consisting of fluoro, chloro, bromo, trifluoromethyl, phenyl and alkyl and alkoxy of from one to six carbon atoms.

Generally, compounds with the same configuration of the 8-and 12-position as the natural PGE$_2$ are preferred. The 9α-hydroxy and 9-keto compounds are preferred as are the compounds with a hydroxyl group at the 11-position. The 15α-hydroxy compounds are also preferred. Hydrogen and p-biphenyl are the preferred identities of R and phenyl and tolyl are preferred as Ar. Among the individual compounds, those for which there is a particular preference are 9α-hydroxy and 9-oxo-5-(2-carboxythiophen-5-yl)-11α, 15α-dihydroxy-16-phenoxy-cis-5-trans-13-α-tetranor-ω-tetranor-prostadienoic acids.

The compounds of the present invention are particularly useful for their ability to induce spasms in the smooth muscle of the uterus and other smooth muscle. Though the spasmogenic activity of the compounds of the present invention are of the order of the activities of PGF$_2$ and PGF$_{2\alpha}$, the present compounds are particularly useful because they have an extremely narrow activity spectrum. The compounds of the present invention are principally smooth muscle stimulants. Other activities exhibited by the natural prostaglandins such as the ability to induce diarrhea, lower systemic blood pressure, dilate bronchioles and inhibit gastric secretion are relatively greatly diminished in the present invention. Nevertheless, their activity as smooth muscle stimulants remains relatively high. The same statements may be made of these compounds if they are compared with 16-aryloxy compounds which do not have a carboxythiophene group terminating the upper side chain.

Useful as intermediates in the preparation of the compounds of the present invention are the optically active compounds of the structure:

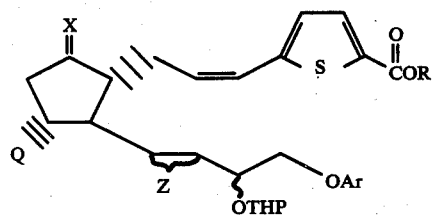

Their optical antipodes and racemic mixtures thereof. Ar, Z, R and X are as defined above. Q is hydrogen or tetrahydropyran-2-yloxy and THP is tetrahydropyran-2-yl. The wavy line at the 15-position indicates that the tetrahydropyran-2-yloxy group may be attached in either the α- or the β-configuration. By carrying out various oxidations, reductions and solvolyses described below, the above compounds are compounds that are converted into pharmaceutically active prostaglandins with a keto or α- or β-hydroxy group at each of the 9- and 15-positions and an α-hydroxy group or a hydrogen atom at the 11α-position.

Another useful intermediate in the synthesis of the compounds of the present invention is the phosphonium salt of the structure:

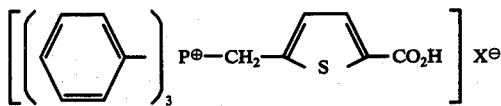

in which X is chloro, bromo or iodo.

Treatment of this compound with a strong base such as sodium methylsulfinylmethide and subsequent contact with γ-lactone

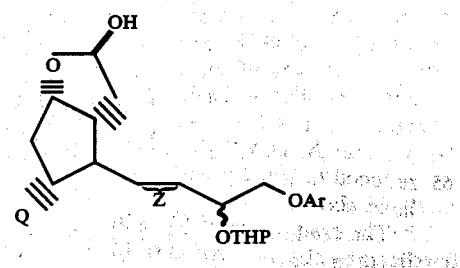

yields compounds of the structure

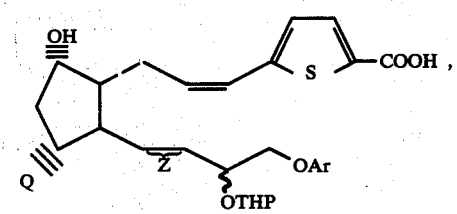

one of the first-mentioned intermediates above. Oxidation with Jones reagent yields the corresponding 9-keto compound and reduction of the 9-keto compound gives an epimeric mixture of 9α- and 9β-hydroxy compounds which may be resolved by column chromatography.

DETAILED DESCRIPTION OF THE INVENTION

As shown in Scheme A, the first step in the synthesis of the 11-desoxy compounds of the present invention (1→2) is a condensation between the known aldehyde 1 (Corey and Ravindranathan, Tetrahedron Lett., 1971, 4753) with an appropriate 3-keto phosphonate to produce enone 2. The keto phosphonate is usually produced by condensation of the appropriate carboxylic acid ester with a dialkyl methyl phosphonate. Typically the desired methyl ester is condensed with dimethyl methyl phosphonate.

Enone 2 is then reduced to enol 3 with zinc borohydride or a hindered alkyl borohydride such as lithium triethylborohydride or potassium tri-sec-butylborohydride. This reduction produces a mixture of epimers both of which may be used as substrates for further reactions. The 3 is used to produce prostaglandin analogs having a α-hydroxyl at C$_{15}$. The epimer of 3 is used to produce prostaglandin analogs having a β-hydroxy at C$_{15}$. In addition, the mixture of C$_{15}$ epimers may be used to produce 15-keto prostaglandin analogs. The epimers produced in the hydride reduction can be separated by column, preparative thin layer, or preparative high pressure liquid chromatography. In the reduction reaction ethers such as tetrahydrofuran or 1,2-dimethoxyethane or acetonitrile are usually employed as solvents.

Enone 2 may be reduced catalytically with hydrogen to ketone 6, a suitable starting material for the preparation of 13,14-dihydro prostaglandin analogs of the present invention. This reduction may be achieved with either a homogeneous catalyst such as tris-tri-phenylphosphinerhodiumchloride or with a heterogeneous catalyst system such as platinum, palladium or rhodium. The stage at which the reduction is carried out is not critical as will be seen below.

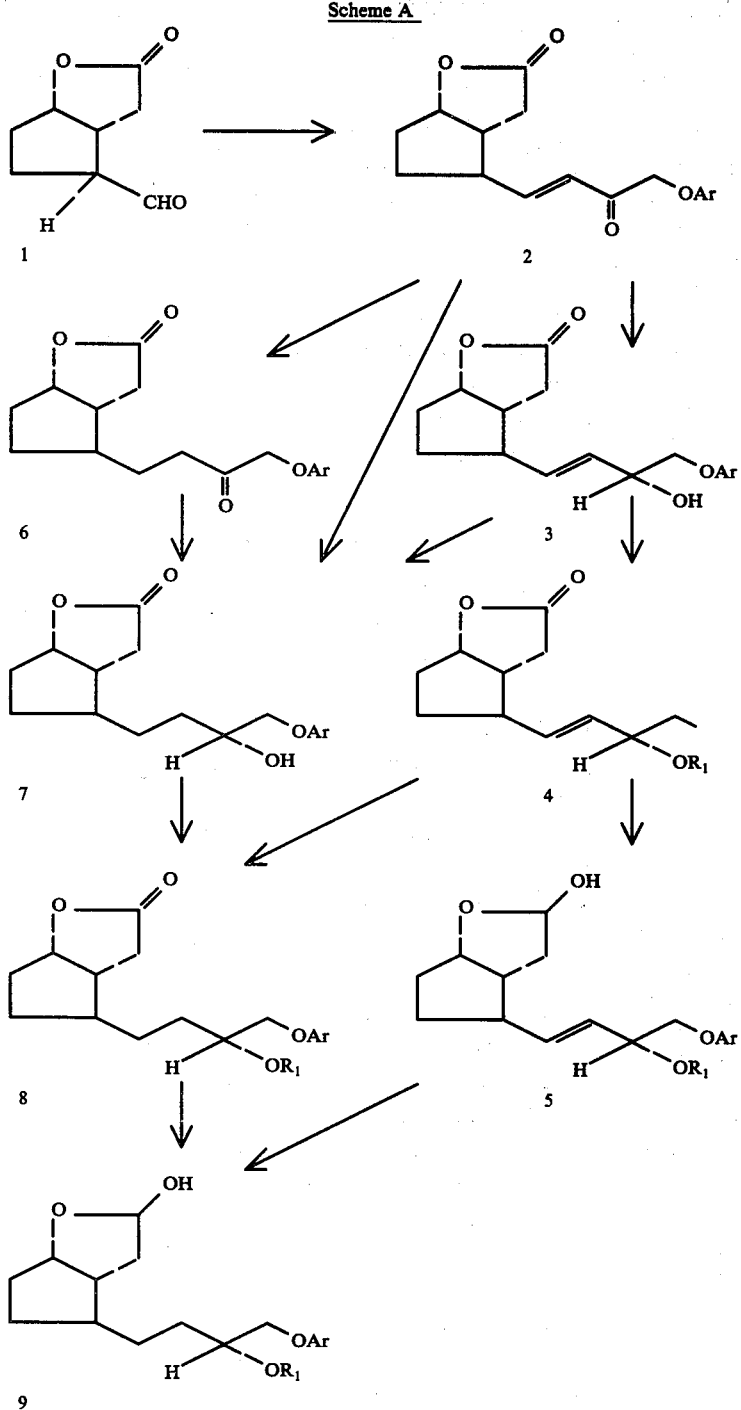

Scheme A

Enone 2 may also be reduced with borohydride ion to produce a mixture of the alcohol 7 and its $C_{15}$ epimer in a single step or alternatively, enol 3 may be catalytically reduced to produce the same epimer mixture.

(3 → 4) involves the protection of the free hydroxyl group with an acid labile protecting group ($R_1$). Any sufficiently acid labile group is satisfactory, however, the most usual ones are tetrahydropyranyl or dimethyl-tert-butylsilyl which can be incorporated in molecule by treatment with dihydropyran and an acid catalyst, usually p-toluenesulfonic acid, in an anhydrous medium or dimethyl-tert-butylsilyl chloride and imidazole, respectively.

(4 → 5) is a reduction of the lactone 4 to hemiacetal 5 using a suitable reducing agent such as disobutyl aluminum hydride in an inert solvent. Low reaction temperatures are preferred and −60° to −80° C. are usual. However, higher temperatures may be employed if over reduction does not occur. 5 is then purified if desired by column chromatography. As indicated in Scheme A, compounds 4 and 5 may be catalytically reduced to 8 and 9 respectively, by the procedure outlined above.

The conversion of (6 → 9) follows that already outlined by the conversion of (2 → 5).

The remainder of the synthesis of the two-series prostaglandin analogs of this invention is outlined in Scheme B. (5 → 10) is a Wittig condensation in which hemiacetal 5 is reacted with (2-carboxythiophen-5-yl-methyl)triphenylphosphonium bromide in dimethyl sulfoxide in the presence of sodium methylsulfinyl methide.

The phosphonium salt is prepared by contacting substantially equimolar amounts of triphenylphosphine and 5-bromomethylthiophene-2-carboxylic acid in a reaction-inert solvent such as acetonitrile at reflux temperatures until the reaction is substantially complete. The precipitated product is collected by filtration and recrystallized from a minimum amount of a suitable solvent or solvent system such as ethanol:hexane and air dried. 10 is then purified as above. The conversion of 10 → 11 is an acid catalyzed hydrolysis of protecting group. Any acid may be used which does not cause destruction of the molecule in the course of the removal of the protecting group, however, this is accomplished most often by the use of 65% aqueous acetic acid. Alternatively, the dimethyl-tert-butylsilyl protecting group may be removed by the action of tetraalkylammonium fluoride in a solvent such as tetrahydrofuran. The product is purified as above.

11 is an 11-desoxy-16-aryloxy-ω-tetranorprostaglandin of the $F_{2\alpha}$ series. The prostaglandin analogs of the $E_2$ series of this invention (13) are prepared from intermediate 10 which may be oxidized by any reagent capable of oxidizing hydroxyl groups which does not attack double bonds. However, the Jones reagent is usually preferred. The product is purified as above to produce intermediate 12. Intermediate 12 may be converted into the prostaglandin analogs of the $E_2$ series (13) of this invention in the same manner as described for (10 → 11). Furthermore, intermediate 12 may be reduced with sodium borohydride to a mixture of intermediates 15 and 10 which are separable by column, preparative thin layer, or preparative high pressure liquid chromatography and which can be converted into prostaglandin analogs of the $F_{2\alpha}$ and $F_{2\beta}$ series of this invention by the methods given for (10 → 11). Alternatively, compound 13 may be reduced with sodium borohydride to provide the $F_{2\alpha}$ and $F_{2\beta}$ prostaglandin analogs of this invention directly. This epimeric mixture may be separated as described above for 15 to provide pure $PGF_{2\alpha}$ and $PGF_{2\beta}$.

The conversion of 9 into the 13,14-dihydro-2-series analogs of the present invention follows that already outlined by the conversion of 5 into 11, 13 and 14.

Scheme B

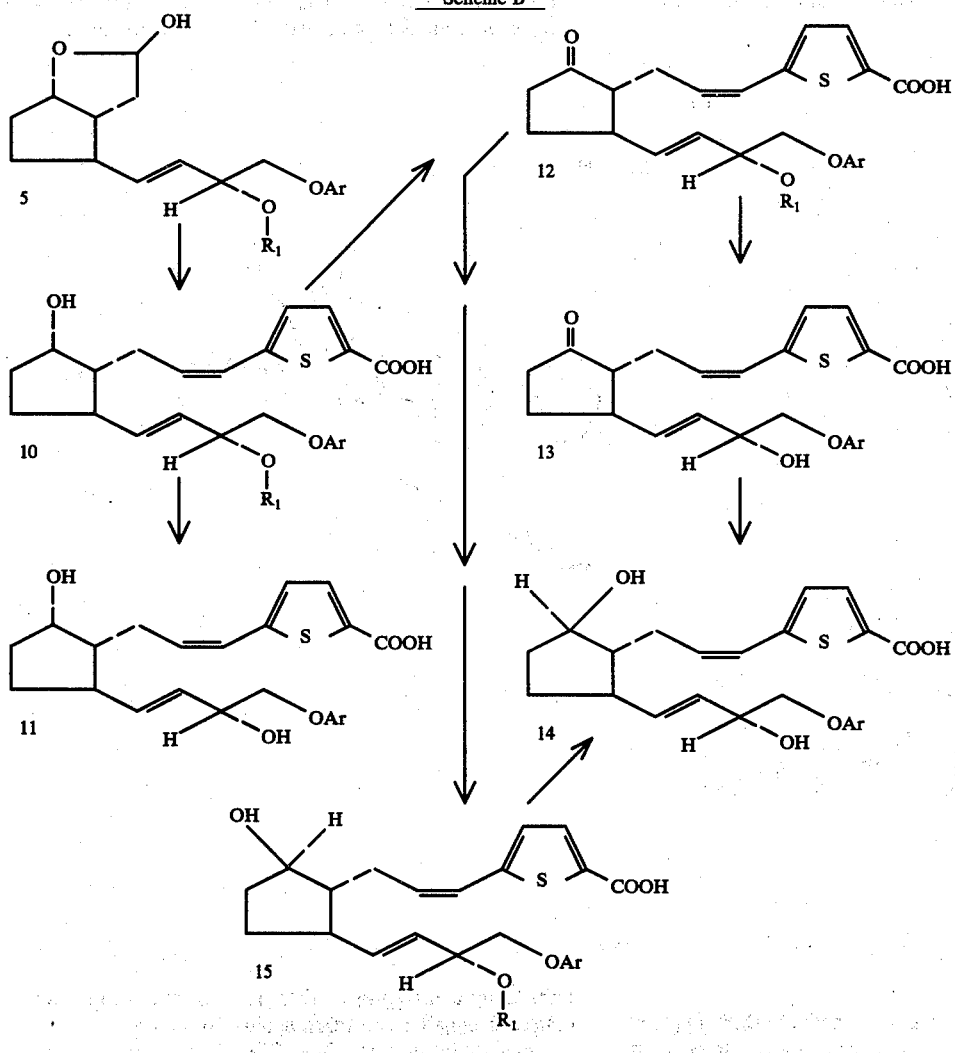

The preparation of the 11-hydroxy compounds of the present invention is shown in Scheme C. In 16 → 17 the ketophosphonate prepared as described above is caused to react with the known [Corey et al., J. Am. Chem. Soc., 93, 1491 (1971)]aldehyde 16 to produce, after chromatography or crystallization, the enone 17.

The enone 17 can be reduced with zinc borohydride or with trialkylborohydrides, such as lithium triethylborohydride, to a mixture of epimeric alcohols, which can be separated as above. Only the α epimer 18 is shown. If the β epimer is used in its place in the following synthesis, one will produce the corresponding 15β-hydroxy prostaglandins. In this reaction ethers such as tetrahydrofuran or 1,2 dimethoxy ethane or acetonitrile are usually employed as solvents.

Further transformations of 18 are shown on Scheme D.

18 → 19 is a base catalyzed transesterification in which the p-biphenyl-carbonyl protecting group is removed. This is most conveniently conducted with potassium carbonate in methanol or methanol-tetrahydrofuran solvent. 19 → 20 involves the protection of the two free hydroxyl groups with an acid-labile protecting group. Any sufficiently acid-labile group is satisfactory; however, the most usual one is tetrahydropyranyl, which can be incorporated in the molecule by treatment with dihydropyran and an acid catalyst in an anhydrous medium. The catalyst is usually p-toluenesulfonic acid.

21 → 22 is a Wittig condensation in which hemiacetal 21 is reacted with (2-carboxythiophen-5-ylmethyl)triphenylphosphonium bromide in dimethyl sulfoxide, in the presence of sodium methylsulfinyl methide. 22 is purified as above.

The conversion 22 → 25 is an acidic hydrolysis of the tetrahydropyranyl groups. Any acid may be used which does not cause destruction of the molecule in the course of the removal of the protecting groups, however, this is acomplished most often by use of 65% aqueous acetic acid. The product is purified as above.

22 → 23 is an oxidation of the secondary alcohol 22 to the ketone 23. This may be accomplished using any oxidizing agent which does not attack double bonds; however, the Jones reagent is usually preferred. The product is purified as above.

23 → 24 is carried out in the same manner as 22 → 25. The product is purified as above.

The 15-keto compounds of the present invention are prepared dissolving the corresponding PGE$_2$ or PGF$_2$ compound in a reaction-inert solvent such as benzene or toluene. To the reaction mixture manganese dioxide is added in an amount approximately one to ten times the weight of the prostaglandin and the reaction stirred at a temperature of from about 10° to 80° C. until the reaction is substantially complete. The reaction mixture is

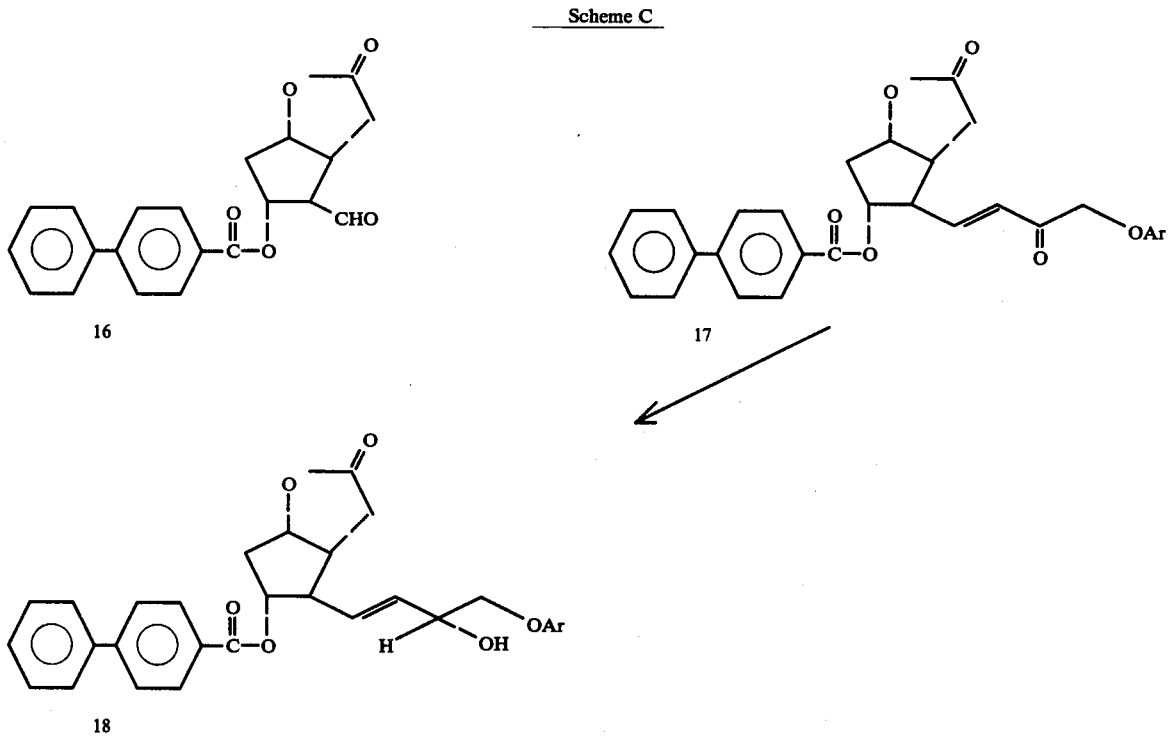

Scheme C

20 → 21 is a reduction of the lactone 20 to the hemiacetal 21 using diisobutyl aluminum hydride in an inert solvent. Low reaction temperatures are preferred and −60° to −70° C. are usual. However, higher temperature may be employed if over-reduction does not occur. 21 is purified, if desired, by column chromatography.

then filtered and evaporated to yield the crude product which is purified by column chromatography.

The 13,14-dihydro PGE$_2$ or PGF$_{2\alpha}$ compounds of the present invention are prepared from the hemiacetal 26 following procedures already outlined by the conversion of 21 into 25, 24 and 27. The hemiacetal 26 may be prepared from 17, 18, 19 or 20 as described above.

Scheme D

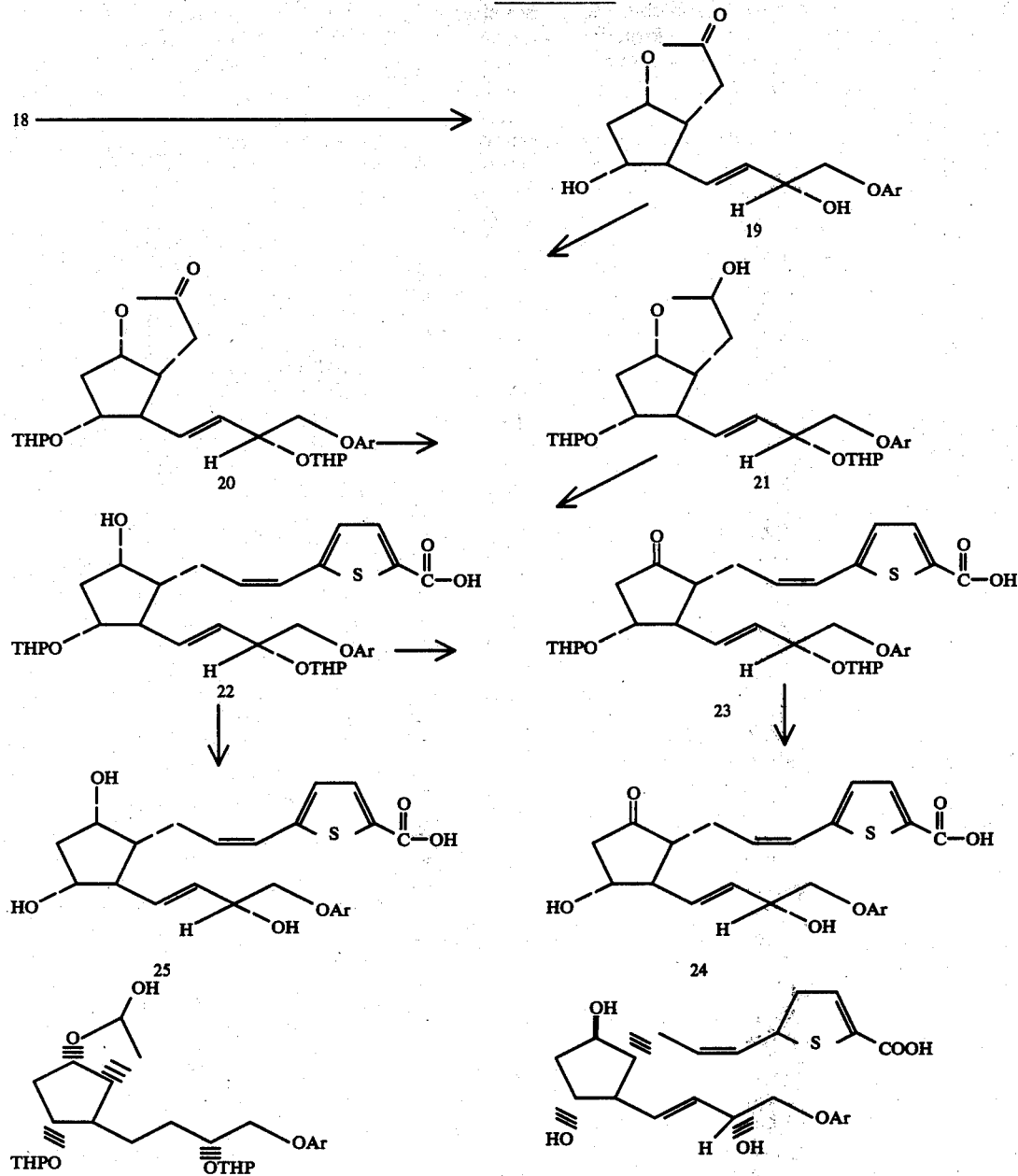

The PGF$_{62}$ compounds of the present invention may be prepared from 23 or 24 by procedures described above for 12 or 13 into 14.

The assignment of the configuration of C15 is made on the basis of mobilities in thin layer chromatography of the alcohols 3 and C15-epi-3 and 18 and C$_{15}$-epi-18. It is assumed that the less polar (higher R$_f$) epimer has the 15α-hydroxy configuration and the more polar (lower R$_f$) epimer has the 15β-hydroxy configuration. Among the suitable solvent systems are mixtures of ether or ethyl acetate in benzene. This assignment of C$_{15}$ configuration is based on that observed for the synthesis of the natural prostaglandins (Corey, et al., J. Am. Chem. Soc., 93, 1491 (1971).

Similarly, the assignment of the configuration of C$_9$ is made on the basis of mobilities in thin layer chromatography of the alcohols 11 and 14 and 25 and 27. It is assumed that the less polar (higher R$_f$) epimer has the 9α-hydroxy configuration and the more polar (lower R$_f$) epimer has the 9β-hydroxy configuration. Among the suitable solvent systems are mixtures of methylene chloride or chloroform and methanol. This assignment of C$_9$ configuration is based on analogy with the natural prostaglandins (Green and Samuelsson, J. Lipid Res., 5, 1A (1964)).

Phenyl and substituted phenyl esters of the present invention are prepared by contacting a prostanoic acid with an appropriate phenol in reaction-inert solvent such as dry methylene chloride in the presence of a coupling agent such as dicyclohexylcarbodiimide or diethylcarbodiimide. For instance, 5-(carboxythiophen- 2-yl)-9-oxo-11α,15α-dihydroxy-16-phenoxy-cis-5-trans-13α-tetranor-ω-tetranorprostadienoic acid may be contacted with p-phenylphenol in dry methylene chloride in the presence of dicyclohexylcarbodiimide to form the corresponding ester. Alkyl and phenylalkyl esters of the present invention may be prepared by contacting a prostanoic acid with an appropriate diazoalkane in a reaction-inert solvent such as ether or tetrahydrofuran. Alternatively, the esters of the present invention may be prepared by first contacting a prostanoic acid with pivaloyl chloride in a reaction inert solvent such as ether in the presence of an appropriate base such as triethylamine and then treating the resultant intermediate with an appropriate alcohol.

In the foregoing procedures, where purification by column chromatography is desired, appropriate chromatographic supports include neutral alumina and silica gel. The chromatography is suitably conducted in reaction-inert solvents such as ether, ethyl acetate, benzene, chloroform, methylene chloride, cyclohexane and n-hexane, as further illustrated in the appended examples. Where purification by high pressure liquid chromatography is desired, appropriate supports include 'Corasil', 'Porasil', and 'Lichrosorb' with inert solvents such as ether, chloroform, methylenechloride, cyclohexane and n-hexane being employed.

It will be seen that the foregoing formulae depict optically active compounds. It is intended that both optical antipodes, e.g. 8,12-nat and 8,12-ent, be embraced by the foregoing formulae and in the appended claims. The two optical antipodes are readily prepared by the same methods by mere substitution of the appropriate optically active precursor aldehyde. It will be clear, however, that the corresponding racemates will exhibit valuable biological activity by virtue of their content of the above-mentioned biologically active optical isomers, and it is intended that such racemates also be embraced by the foregoing formulae herein and in the appended claims. The racemic mixtures are readily prepared by the same methods employed herein to synthesize the optically active species, by mere substitution of corresponding racemic precursors in place of optically active starting materials.

In numerous in vivo and in vitro tests we have demonstrated that the new prostaglandin analogs possess physiological activities comparable but much more tissue selective and longer acting than those exhibited by the natural prostaglandins (see above). These tests include, among others, a test for effect on dog blood pressure, inhibition of stress-induced ulceration in the rat, effect on mouse diarrhea, inhibition of stimulated gastric acid secretion in rats and dogs, spasmogenic effect on isolated guinea pig and rat uterus, protective effect on histamine induced bronchospasm in the guinea pig, and antifertility activity in rats and guinea pigs.

The physiological responses observed in these tests are useful in determining the utility of the test substance for the treatment of various natural and pathological conditions. Such determined utilities include: vasodilator activity, antihypertensive activity, bronchodilator activity, antiarrythmic activity, cardiac stimulant activity, antifertility activity, antiulcer activity and antisecretory activity.

An advantage possessed by 11-desoxy prostaglandins of the E series in general is their increased stability as compared with such as $PGE_2$. In addition, the novel prostaglandin analogs of this invention possess highly selective activity profiles compared with the corresponding naturally occurring prostaglandins and, in many cases, exhibit a longer duration of action. The novel prostaglandin analogs of this invention possess useful antifertility activity. Prime examples of the therapeutic importance of these prostaglandin analogs is the efficacy of 5-(2-carboxythiophen-5-yl)-9α, 11α, 15α-trihydroxy-16-phenoxy-cis-5-trans-13-α-tetranor-ω-tetranorprostadienoic acid and the corresponding 9-oxo compound which exhibit excellent antifertility activity. At the same time, other physiological activities are markedly depressed in comparison with $PGE_2$.

Pharmacologically acceptable salts useful for the purposes described above are those with pharmacologically acceptable metal cations, ammonium, amine cations, or quaternary ammonium cations. Salts can be formed with the acids of the present invention.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, epherdrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The new compounds of this invention can be used in a variety of pharmaceutical preparations which contain the compound or a pharmaceutically acceptable salt thereof, and they may be administered in the same manner as natural prostaglandins by a variety of routes, such as intravenous, oral and topical, including aerosol, intravaginal, and intranasal, among others.

For induction of abortion, tablets or an aqueous suspension or alcoholic solution of a compound of the present invention would appropriately be administered at oral doses of about 0.1–20 mg., with 1–7 doses per day being employed. For intravaginal administration a suitable formulation would be lactose tablets or an impregnated tampon of the same agent. For such treatments suitable doses would be from about 0.1–20 mg/dose with 1–7 doses being employed. For intraamniotic administration a suitable formulation would be an aqueous solution containing 0.05–10 mg/dose with 1-7 doses being employed. For extra-amniotic administration a suitable formulation would be an aqueous solution containing 0.005-1 mg/dose with 1-5 doses being employed. Alternatively, these compounds can be infused intravenously for induction of abortion at doses of 0.05-50 μg/minute for a period of from about 1-24 hours.

Another use for the novel compounds of the present invention is as an inducer of labor. For this purpose an ethanol-saline solution is employed as an intravenous infusion in the amount of from about 0.1-10 μg/kg/min for from about 1-24 hours.

These compounds may also be used for fertility control. For this purpose a tablet is employed for intravaginal or oral administration containing 0.1-20 mg. of prostaglandin per dose with 1-7 doses being employed at or following the expected day of menstruation. For synchronization of the estrous cycle in pigs, sheep, cows or horses, a solution or suspension containing 0.03-30 mg/dose of the compound is administered intramuscularly from 1-4 days.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol, and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims. In these examples it will be appreciated that all temperatures are expressed in Centigrade, all melting and boiling points are uncorrected.

EXAMPLE I

Dimethyl 2-Oxo-3-phenoxypropylphosphonate

A solution of 33.2 g (268 mmoles) dimethyl methylphosphonate (Aldrich) in 360 ml dry tetrahydrofuran was cooled to −78° in a dry nitrogen atmosphere. To the stirred phosphonate solution was added 118 ml of 2.34 M n-butyllithium in hexane solution (Alfa Inorganics, Inc.) dropwise over a period of 18 minutes at such a rate that the reaction temperature never rose above −65°. After an additional 5 minutes stirring at −78°, 22.2 g (134 mmole) methyl 2-phenoxy acetate was added dropwise at a rate that kept the reaction temperature less than −70° (20 minutes). After 3.5 hours at −78° the reaction mixture was allowed to warm to ambient temperature, neutralized with 14 ml acetic acid and rotary evaporated to a white gel. The gelatinous material was taken up in 175 ml water, the aqueous phase extracted with 100 ml portions of chloroform (3x), the combined organic extracts were backwashed (50 cc H₂O), dried (MgSO₄), and concentrated (water aspirator) to a crude residue and distilled, b.p. 172°-175° (0.5 mm) to give 24.6 g dimethyl 2-oxo-3-phenoxypropylphosphonate.

The nmr spectrum (CDCl₃) showed a doublet centered at 3.75δ (J = 11.5 cps, 6H) for

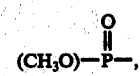

a singlet at 4.7δ (2H) for C₆H₅O-CH₂-CO-, a doublet centered at 3.24δ (J = 23 cps, 2H)

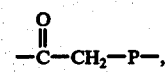

and a multiplet at 6.8-7.5δ (5H) for the aromatic protons.

EXAMPLE II

Dimethyl 2-Oxo-3-(m-tolyloxy)propylphosphonate

A solution 69.4 g. (.555 moles) dimethyl methylphosphonate (Aldrich) in 800 ml. dry tetrahydrofuran was cooled to −78° in a dry nitrogen atmosphere. To the stirred phosphonate solution was added 230 ml. of 2.4m n-butyllithium in hexane solution (Alfa Inorganics) dropwise over a period of 75 min. at such a rate that the reaction temperature did not rise above −65°. After an additional 5 min. at −78°, 50 g. (.277 mole) methyl 2-(m-tolyloxy) acetate was added rapidly (5 min.). After 3.5 hrs. at −78°, the reaction mixture was allowed to warm to ambient temperature, neutralized with 50 ml. acetic acid and rotary evaporated to a white gel. The gelatinous material was taken up in 175 ml. water, the aqueous phase extracted with 100 ml. portions of chloroform (3x), the combined organic extracts were backwashed (50 cc H₂O), dried and concentrated to a crude residue and distilled, b.p. 159°-164° (0.15 mm) to give 40 g. dimethyl 2-oxo-3-(m-tolyloxy)propylphosphonate.

The nmr spectrum (CDCl₃) showed a doublet centered at 3.75 δ (J=11.5 cps, 6H) for

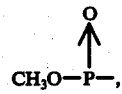

a singlet at 4.70 δ (2H) for C₇H₈-O-CH₂-CO-, a doublet centered at 3.24 δ (J=23 cps, 2H) for

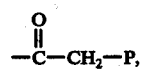

a singlet at 2.30 δ (3H) for the methyl and a multiplet at 6.8-7.5 δ (4H) for the aromatic protons.

In similar fashion, a series of 2-oxo-3-(aryloxy)-propylphosphonates may be prepared in which any of the above-mentioned Ar is the aryl substituent. For example, Ar may be

| Ar | Ar |
| --- | --- |
| p-biphenyl | p-bromophenyl |
|  | o-chlorophenyl |
| p-tolyl | p-ethoxyphenyl |
| p-trifluoromethylphenyl | p-fluorophenyl |
| α-naphthyl | p-ethylphenyl |
| β-naphthyl | o-methoxyphenyl |
| p-methoxyphenyl | m-methoxyphenyl |
| o-fluorophenyl | m-fluorophenyl |
| p-chlorophenyl | p-isopropylphenyl |
| m-biphenyl | p-butylphenyl |
| m-ethylphenyl | m-trifluoromethylphenyl |
| m-chlorophenyl | o-bromophenyl |
| o-tolyl | o-bromophenyl |

-continued

| Ar | Ar |
|---|---|
| o-trifluoromethylphenyl | p-isopropoxyphenyl |

EXAMPLE III

2-[3α-p-Phenylbenzoyloxy-5α-hydroxy-2β-(3-oxo-4-phenoxy-trans-1-buten-1-yl)cyclopent-1α-yl]Acetic Acid, γ-lactone (17)

Dimethyl 2-oxo-3-phenoxypropylphosphonate (5.4 g), 21 mmole) in 200 ml anhydrous ether was treated with 7.9 ml (19 mmole) 2.5 M n-butyllithium in n-hexane (Alfa Inorganics, Inc.) in a dry nitrogen atmosphere at room temperature. After 5 min. of stirring, an additional 400 ml. of anhydrous ether was added followed by 6.0 g (17 mmole) 2-[3α-p-phenylbenzoyloxy-5α-hydroxy-2β-formylcyclopent-1α-yl]acetic acid,γ-lactone (16) in one portion and 50 ml anhydrous ether. After 35 minutes the reaction mixture was quenched with 5 ml glacial acetic acid and washed with 100 ml saturated sodium bicarbonate solution (4 x), 100 ml water (2 x), 100 ml saturated brine (1 x), dried (MgSO$_4$) and evaporated to yield 5.2 gm 2-[3α-p-phenylbenzoyloxy-5α-hydroxy-2β-(3-oxo-4-phenoxy-trans-1-buten-1-yl)cyclopent-1α-yl]acetic acid, γ-lactone (17) as a solid after column chromatography (Silica gel, Baker, 60-200 mesh); m.p. 112°-114° after crystallization from methylene chloridehexane.

The ir spectrum (KBr) of the product exhibited absorption bands at 1775 cm$^{-1}$ (strong), 1715 cm$^{-1}$ (strong), 1675 cm$^{-1}$ (medium) and 1630 cm$^{-1}$ (medium) attributable to the carbonyl groups and at 970 cm$^{-1}$ for the trans double bond.

In a similar fashion, the phosphonates of Example II may be reacted with the γlacetone aedehyde.

EXAMPLE IV 2-(3α-p-Phenylbenzoyloxy-5α-hydroxy-2β-(3α-hydroxy-4-phenoxy-trans-1-buten-1-yl) cyclopent-1α-yl]acetic acid, γ-lactone (18)

To a solution of 5.1 g (10.5 mmole) 2-[3α-p-phenylbenzoyloxy 5α-hydroxy-2β-(3-oxo-4-phenoxy-trans-1-buten-1-yl)cyclopent-1α-yl] acetic acid, γ-lactone (17) in 30 ml dry 1,2-dimethoxyethane in a dry nitrogen atmosphere at ambient temperature was added dropwise 11 ml (5.5 mmole) of a 0.5 M zinc borohydride solution. After stirring at room temperature for 2 hours, a saturated sodium bitartrate solution was added dropwise until hydrogen evolution ceased. The reaction mixture was allowed to stir for 5 minutes at which time 250 ml dry methylene chloride was added. After drying (MgSO$_4$) and concentrating (water aspirator) the resultant semisolid was purified by column chromatography on silica gel (Baker "Analyzed" Reagent 60-200 mesh) using ether as eluent. After elution of less polar impurities a fraction containing 896 mg 2-[3α-p-phenylbenzoyloxy-5α-hydroxy-2β-(3α-hydroxy-4-phenoxy-trans 1-buten-1-yl)cyclopent-1α-yl]acetic acid, γ-lactone, (18) a 600 mg fraction of mixed 18 and epi-18 and finally a fraction (1.5 gm) of 2-[3α-p-phenylbenzoyloxy-5α-hydroxy-2β-(3β-hydroxy-4-phenoxy-trans-1-buten-yl)cyclopent-1α-yl]acetic acid, γ-lactone (epi-18).

The ir spectrum (CHCl$_3$) of 4 had strong carbonyl absorptions at 1770 and 1715 cm$^{-1}$ and an absorption at 970 cm$^{-1}$ for the trans double bond.

In a similar fashion the other compounds of Example III may be reduced with zinc borohydride.

The 15-epi product of this Example may be converted into the 15-eip prostaglandin analogs of this invention by the procedures of Examples V-VII, IX-XIIΔ XVII-XX, and XXI°.

EXAMPLE V

2-[3α, 5α-Dihydroxy-2β-(3α-hydroxy-4-phenoxy-trans-1-buten-1-yl) cyclopent-1α-yl]acetic acid, γ-lactone (19)

A heterogeneous mixture of 846 mg (1.7 mmole) of 2-[3α-p-phenylbenzoyloxy-5α-hydroxy-2β-(3α-hydroxy-4-phenoxy-trans-1-buten-1-yl)cyclopent-1α-yl]acetic acid, γ-lactone (18) 10 ml of absolute methanol and 120 mg of finely powdered, anhydrous potassium carbonate was stirred at room temperature for 20 hours, then cooled to 0°. To the cooled solution was added 1.75 ml of 1.0N aqueous hydrochloric acid. After stirring at 0° for an additional 10 minutes, 10 ml. of water was added with concomitant formation of methyl p-phenyl-benzoate which was collected by filtration. The filtrate was saturated with solid sodium chloride, extracted with ethyl acetate (4 × 10 ml.), the combined organic extracts were washed with saturated sodium bicarbonate (10 ml.) dried (MgSO$_4$) and concentrated to give 445 mg of viscous, oily 2-[3α,5α-dihydroxy-2β-(3α-hydroxy-4-phenoxy-trans-1-buten-1-yl)cyclopent-1α-yl]acetic acid, γ-lactone (19).

The ir spectrum (CHCl$_3$) exhibited a strong absorption at 1772 cm$^{-1}$ for the lactone carbonyl and medium absorption at 965 cm$^{-1}$ for the trans-double bond.

In a similar fashion, one may solvolyze the other compounds of Example IV.

EXAMPLE VI

2-[5α-Hydroxy-3α-(tetrahydropyran-2-yloxy)-2β-(3α-tetrahydropyran-2-yloxy)-4-phenoxy-trans-1-buten-1-yl)cyclopent-1α-yl]acetic acid, γ-lactone (20)

To a solution of 445 mg (1.46 mmole) 2-[3α,5α-dihydroxy-2α-(3α-hydroxy-4-phenoxy-trans-1-buten-yl)cyclopent-1α-yl]acetic acid, γ-lactone (19) in 5 ml anhydrous methylene chloride and 0.4 ml of 2,3-dihydropyran at 0° in a dry nitrogen atmosphere was added 5 mg p-toluenesulfonic acid, monohydrate. After stirring for 15 minutes, the reaction mixture was combined with 100 ml ether, the ether solution washed with saturated sodium bicarbonate (1 × 15 ml) then saturated brine (1 × 15 ml), dried (MgSO$_4$) and concentrated to yield 752 mg (>100%) crude 2-[5α-hydroxy-3α-(tetrahydropyran-2-yloxy-2β-(tetrahydropyran-2-yloxy)-4-phenoxy-trans-1-buten-1-yl)cyclopent-1α-yl]acetic acid, γ-lactone (20).

The ir (CHCl$_3$) spectrum had a medium absorption at 970 cm$^{-1}$ for the trans-double bond, and at 1770 cm$^{-1}$ for lactone carbonyl.

The other compounds of Example V may, in a similar fashion, be contacted with 2,3-dihydropyran.

The product of this Example may be catalytically hydrogenated by the procedure of Example XXIV to provide 2-[5α-hydroxy-3α-(tetrahydropyran-2-yloxy)-2β-(3α-(tetrahydropyran-2-yloxy)-4-phenoxybut-1-yl)cyclopent-1α-yl]acetic acid, γ-lactone which may be converted into the 13,14 -dihydroprostaglandin two-series analogs of this invention by the procedures of Examples VII, IX-XII, XVII-XX and XI-XXII.

EXAMPLE VII

2[5α-Hydroxy-3α-(tetrahydropyran-2-yloxy)-2β-(3α-tetrahydropyran-2-yloxy)-4-phenoxy-trans-1-buten-1-yl)cyclopent-1α-yl] acetaldehyde, γ-hemiacetal (21)

A solution of 690 mg (1.46 mmole) 2-[5α-hydroxy-3α-(tetrahydropyran-2-yloxy)-2β-(3α-(tetrahydropyran-2-yloxy)-4-phenoxy-trans-1-buten-1-yl)cyclopent-1α-yl]acetic acid, γ-lactone (20) in 8 ml dry toluene was cooled to −78° in a dry nitrogen atmosphere. To this cooled solution was added 2.0 ml of 20% diisobutylaluminum hydride in n-hexane (Alfa Inorganics) dropwise at such a rate so that the internal temperature never rose above −65° (15 minutes). After an additional 45 minutes of stirring at −78°, anhydrous methanol was added until gas evolution ceased and the reaction mixture was allowed to warm to room temperature. The reaction mixture was combined with 100 ml ether, washed with 50% sodium potassium tartrate solution (4 × 20 ml), dried ($Na_2SO_4$) and concentrated to yield 613 mg 2-[5α-hydroxy-3α-(tetrahydropyran-2-yloxy)-2β-(3α-(tetrahydropyran-2-yloxy)-4-phenoxy-trans-1-buten-1-yl)cyclopent-1-yl]acetaldehyde, γ-hemiacetal (21)

One may reduce the other compounds of Example VI in a similar fashion with diisobutylaluminum hydride.

EXAMPLE VIII (2-Carboxythiophen-5-yl-methyl)triphenylphosphonium bromide

A mixture of 2.54 g. (11.5 mmoles) of 5-bromomethylthiophene-2-carboxylic acid and 3.02 g. of triphenylphosphine in 50 ml. of acetonitrile was heated at reflux for 1.5 hours then was cooled. The resultant precipitate was collected by filtration and was recrystallized from ethanol:hexane to provide the (2-carboxythiophen-5-yl-methyl)triphenylphosphonium bromide weighing 3.16 g. and melting at 273°.

Anal. calcd.: C, 59.64; H, 4.17; S, 6.63; Br, 16.53; P, 6.40. Found: C, 59.76; H, 4.32; S, 6.99; Br, 16.30; P, 6.66.

EXAMPLE IX 5-(2-Carboxythiophen-5-yl)-9α-hydroxy-11α,15α-bis-(tetrahydropyran-2-yloxy)-16-phenoxy-cis-5-trans-13-ω-tetranor-α-tetranorprostadienoic acid (22)

To a solution of 2.09 g. (4.31 mmole) (2-carboxythiophen-5-yl-methyl)triphenylphosphonium bromide in a dry nitrogen atmosphere in 5.0 ml. dry dimethyl sulfoxide was added 4.3 ml. (8.6 mmole) of a 2.0 M solution of sodium methylsulfinylmethide in dimethyl sulfoxide. To this red ylide solution was added dropwise a solution of 0.82 g. (1.73 mmole) 2-[5α-hydroxy-3α-(tetrahydropyran-2-yloxy)-2β-(3α-tetrahydropyran-2-yloxy]-4-phenoxy-trans-1-buten-1-yl)cyclopent-1α-yl]acetaldehyde, γ-hemiacetal (21) in 5.0 ml. dry dimethyl sulfoxide over a period of 45 minutes. After an additional 15 minutes stirring at room temperature, the reaction mixture was poured onto ice water. The basic aqueous solution was acidified to pH∼3 with 10% aqueous hydrochloric acid. The acidic solution was extracted with ethyl acetate (3x) and the combined organic extracts washed with water (2x), dried ($MgSO_4$) and evaporated to a solid residue. This solid residue was triturated with ether and filtered. The filtrate was concentrated to provide, 2.7 g (>100%) of 5-(2-carboxythiophen-5-yl)-9α-hydroxy-11α, 15α-bis-(tetrahydropyran-2-yloxy)-16-phenoxy-cis-5-trans-13-ω-tetranor-α-tetranorprostadienoic acid which was used without further purification.

The ir spectrum ($CHCl_3$) of the purified product exhibited a strong absorption at 1710 $cm^{-1}$ for the acid carbonyl and a medium absorption at 970 $cm^{-1}$ for the trans double bond.

In a similar fashion, the other compounds of Example VII may be contacted with (2-carboxythiophen-5-yl-methyl)triphenylphosphonium bromide.

EXAMPLE X 5-(2-Carboxythiophen-5-yl)-9α,11α,15α-trihydroxy-16-phenoxy-cis-5-trans-13-ω-tetranor-α-tetranorprostadienoic acid (25)

A solution of 1.35 g. 5-(2-carboxythiophen-5-yl)-9α-hydroxy-11α,15α-bis-(tetrahydropyran-2-yloxy)-16-phenoxy-cis-5-trans-13-ω-tetranor-α-tetranorprostadienoic acid (22) in 6 ml. of a 65:35 mixture of glacial acetic acid:water was stirred under nitrogen at room temperature for 18 hours then was concentrated by rotary evaporation. The resultant crude oil was purified by column chromatography on silica gel (Mallinckrodt CC-7 100-200 mesh) using mixtures of chloroform:ethyl acetate as eluents. After elution of less polar impurities the 5-(2-carboxythiophen-5-yl)-9α,11α,15α-trihydroxy-16-phenoxy-cis-5-trans-13-ω-tetranor-α-tetranorprostadienoic acid (25) was collected as a colorless foam weighing 330 mg.

The ir spectrum (KBr) of the product exhibited a strong absorption at 5.77 μ for the acid carbonyl and a medium absorption at 10.25 μ for the trans double bond.

The other compounds of Example IX are solvolyzed in a similar fashion.

EXAMPLE XI 5-(2-carboxythiophen-5-yl)-9-oxo-11α,15α-bis-(tetrahydropyran-2-yloxy)-16-phenoxy-cis-5-trans-13-ω-tetranor-α-tetranorprostadienoic acid (23)

To a solution cooled to −10° under nitrogen of 1.2 g. 5-(2-carboxythiophen-5-yl)-9α-hydroxy-11α, 15α-bis-(tetrahydropyran-2-yloxy)-16-phenoxy-cis-5-trans-13-ω-tetranor-α-tetranorprostadienoic acid (22) in 10 ml. reagent grade acetone was added dropwise to 0.35 ml of Jones' reagent. After 15 minutes at −10°, 0.35 ml 2-propanol was added and the reaction mixture was allowed to stir an additional 5 minutes at which time it was combined with ethyl acetate, washed with water (2x), dried ($MgSO_4$) and concentrated to give 1.20 g. of 5-(2-carboxythiophen-5-yl)-9-oxo-11α,15α-bis-(tetrahydropyran-2-yloxy)-16-phenoxy-cis-5-trans-13-ω-tetranor-α-tetranorprostadienoic acid (23) which was used without purification.

The other compounds of Example IX may be oxidized in a similar fashion.

The product of this Example may be reduced by the procedure of Example XXI and then hydrolyzed by the procedure of Example X to form the prostaglandin $F_{2α}$ analogs of this invention.

EXAMPLE XII 5-(2-Carboxythiophen-5-yl)-9-oxo-11α,15α-dihydroxy-16-phenoxy-cis-5-trans-13-ω-tetranor-α-tetranorprostadienoic acid (24)

A solution of 1.20 g. 5-(2-carboxythiophen-5-yl)-9-oxo-11α, 15α-bis-(tetrahydropyran-2-yloxy)-16-phenoxy-cis-5-trans-13-ω-tetranor-α-tetranorprostadienoic acid (23) in 6 ml of a 65:35 mixture of glacial acetic acid:water was stirred under nitrogen at room temperature for 18 hours then was concentrated by rotary evaporation. The resultant crude oil was purified by column chromatography on silica gel (Mallinckrodt CC-4 100-200 mesh) using mixtures of chloroform:ethyl acetate as eluents. After elution of less polar impurities the 5-(2-carboxythiophen-5-yl)-9-oxo-11α,15α-dihydroxy-16-phenoxy)-cis-5-trans-ω-tetranor-α-tetranor-prostadienoic acid (24) was collected as a white solid weighing 190 mg. and melting at 144°–146° (from chloroform).

The ir spectrum (KBr) of the product exhibited strong absorptions at 5.68 μ for the ketone carbonyl and at 5.84 μ for the acid carbonyl and a medium absorption at 10.25 μ for the trans double bond.

The other compounds of Example XI may be solvolyzed in a similar manner.

EXAMPLE XIII

2-[5α-Hydroxy-2β-(3-oxo-4-(m-tolyloxy)-trans-1-buten-1-yl) cyclopent-1α-yl]acetic acid, γ-lactone (2)

Dimethyl 2-oxo-3-m-tolyloxy propylphosphonate 8.05 g., (31 mmole), in 100 ml. dry tetrahydrofuran was treated with 1.1 g. (28.6 mmole) sodium hydride (Alfa Inorganics) in a dry nitrogen atmosphere at room temperature. After 50 min. of stirring, a solution of 4 g. (26 mmole) 2-[5α-hydroxy-2β-formylcyclopent-1α-yl]acetic acid, γ-lactone (1) in 25 ml of dry tetrahydrofuran was added dropwise over 10 min. After 30 min. the reaction was quenched with 6 ml. glacial acetic acid, diluted with ether and washed with 100 ml. saturated sodium bicarbonate (2x), 100 ml. water (2x) and 100 ml. saturated brine (1x), dried (Na₂SO₄) and evaporated to yield 4.6 g. 2[5α-hydroxy-2β-(3-oxo-4-(m-tolyloxy)-trans-1-buten-1-yl)cyclopent-1α-yl]acetic acid, γ-lactone (2) as an oil after column chromatography (silica gel, Baker, 60-200 mesh).

The ir spectrum (CHCl₃) of the product exhibited absorption bands at 1775 cm⁻¹ (strong), 1715 cm⁻¹ (strong), 1675 cm⁻¹ (medium) and 1630 cm⁻¹ (medium) attributable to the carbonyl groups and at 970 cm⁻¹ for the trans double bond.

In similar fashion, the other phosphonates of Examples I and II may be reacted with (1) to form the corresponding 2β-substituted Wittig condensation products.

EXAMPLE XIV

2-[5α-Hydroxy-2β-(3α-hydroxy-4-(m-tolyloxy)-trans-1-buten-1-yl)-cyclopent-1α-yl]acetic acid, γ-lactone (3)

To a solution of 4.6 g. (15.3 mmole) 2-[5α-hydroxy-2β-(3-oxo-4-(m-tolyloxy)-trans-1-buten-1-yl)cyclopent-1α-yl]acetic acid, γ-lactone (2) in 50 ml dry tetrahydrofuran was cooled to −78° in a dry nitrogen atmosphere. Lithium triethylborohydride (Aldrich). 16.8 (16 mmole) was added dropwise over 15 min. After stirring at room temperature for 30 min., the reaction was quenched with 10 ml. of aqueous acetic acid and allowed to warm to room temperature. The reaction mixture was concentrated by rotary evaporation, taken up in ether and washed with 100 ml. water (2x) and 100 ml. brine (2x). After drying (Na₂SO₄) and concentrating the resultant oil was purified by column chromatography on silica gel (Baker "Analyzed" Reagent) using ether as eluent. After elution of less polar impurities, a fraction "containing 1.5 g 2-[5α-hydroxy-2β-(3α-hydroxy-4-(m-tolyloxy)-trans-1-buten-1-yl) cyclopent-1α-yl]acetic acid, γ-lactone (3), a 400 mg. fraction of mixed 3 and epi-3 and finally a fraction containing 1.7 g. 2[5α-hydroxy-2β-(3β-hydroxy-4-(m-tolyloxy)-trans-1-buten-1-yl)cyclopent-1α-yl]acetic acid, γ-lactone epi-3 was collected.

The ir spectrum (CHCl₃) of the title compound had strong carbonyl absorbtion at 1770 cm⁻¹ and an absorbtion at 970 cm⁻¹ for the trans double bond.

In a similar fashion, the other compounds of Example XIII may be reduced to an epimeric mixture of 3-hydroxy compounds which may be separated by column chromatography.

The 15-epi product of this Example may be converted into the 11-desoxy-15-epi prostaglandin analog of this invention by the procedures of XV, XVI, IX-XII, and XVII-XXIII.

EXAMPLE XV

2-[5α-Hydroxy-2β-(3α-(tetrahydropyran-2-yloxy)-4-(m-tolyloxy)-trans-1-buten-1-yl)cyclopent-1α-yl]acetic acid, γ-lactone (4) p To a solution of 1.5 g. (4.9 mmole) 2-[5α-hydroxy-2β-(3α-hydroxy-4-(m-tolyloxy)-trans-1-buten-1-yl)cyclopent-1α-yl]acetic acid, γ-lactone (3) in 45 ml. anhydrous methylene chloride and 0.94 ml. of 2,3-dihydropyran at 0° in a dry nitrogen atmosphere was added 15 mg. p-toluenesulfonic acid, monohydrate. After stirring for 30 min., the reaction was diluted with 100 ml. ether and the ether solution washed with saturated sodium bicarbonate (1 × 15 ml.) then saturated brine (1 × 25 ml.), dried (Na₂SO₄) and concentrated to yield 2 g. crude 2-[5α-hydroxy-2β-(3α-(tetrahydropyran-2-yloxy)-4-(m-tolyloxy)-trans-1-buten-1-yl)cyclopent-1α-yl]acetic acid, γ-lactone (4).

The ir (CHCl₃) spectrum had a medium absorbtion at 970 cm⁻¹ for the trans double bond and at 1770 cm⁻¹ for the lactone carbonyl.

In a similar fashion, the α-hydroxy group of the other compounds of Example XIV may be reacted with 2,3-dihydropyran.

EXAMPLE XVI

2-[5α-Hydroxy-2β-(3α-(tetrahydropyran-2-yloxy)-4-(m-tolyloxy)-trans-1-buten-1-cyl)cyclopent-1α-yl]acetaldehyde, γ-hemiacetal (5)

A solution of 2.0 g. (4.95 mmole) 2-[5α-hydroxy-2β-(3α-(tetrahydropyran-2-yloxy)-4-(m-tolyloxy)-trans-1-buten-1-yl)cyclopent-1α-yl]acetic acid, γ-lactone (4) in 50 ml dry toluene was cooled to −78° in a dry nitrogen atmosphere. To this cooled solution was added 6.8 ml. of 20% diisobutylaluminium hydride in n-hexane (Alfa Inorganics) dropwise at such a rate that the internal temperature never rose above −65° (20 min.). After an additional 45 min. of stirring at −78°, anhydrous methanol was added until gas evolution ceased and the reaction mixture was allowed to warm to room temperature. The reaction mixture was combined with 100 ml. ether, washed with 50% sodium potassium tartrate solution (4 × 20 ml.) dried (Na₂SO₄) and concentrated to yield 2.2 g. of crude 2-[5α-hydroxy-2β-(3α-(tetrahydropyran-2-yloxy)-4-(m-tolyloxy)-trans-1-buten-1-yl)cyclopent-1α-yl]acetaldehyde, γ-hemiacetal (5). This crude sample was purified by column chromatography on silica gel (Baker "Analyzed" Reagent) eluting with ether and ethyl acetate affording 1.7 g. of the pure product.

In a similar fashion, the γ-lactones of Example XV may be converted to γ-hemiacetals.

Following the method of Example IX-XII and XVII-XXIII, these compounds may be converted into the 11-desoxy PGE$_2$ and PGF$_2$ analogs of the present invention.

EXAMPLE XVII p-Biphenyl-2-(Carboxythiophen-5-yl)-9-oxo-15α-hydroxy-16-phenoxycis-5-trans-13-α-tetranor-ω-tetranorprostadienoate To a mixture of 400 mg. of (2-carboxythiophen-5-yl)-9-oxo-15α-hydroxy-16-phenoxy-cis-5-trans-13-α-tetranor-ω-tetranorprostadienoic acid and 2.07 g. of p-phenylphenol in 40 ml. of dry methylene chloride is added 11.7 ml. of a 0.1M solution of [1-(3-dimethylaminopropyl)]-3-ethylcarbodiimide in methylene chloride. The mixture is stirred at room temperature for 20 hours under nitrogen and is then concentrated. The solid residue is purified by silica gel (Baker "Analyzed"60-200 mesh) chromatography using mixtures of chloroform:benzene as eluents. After removal of less polar impurities the title compound is eluted.

In a similar fashion, the compounds of Examples X, XII, XVI and XXI-XXIII may be converted to the p-biphenyl esters.

Using the above procedure, these acids may be converted to other aryl esters by employing, among others, the following phenols

| | |
|---|---|
| p-chlorophenol | m-ethoxyphenol |
| m-methoxyphenol | p-iodophenol |
| p-isopropylphenol | p-(t-butyl)phenol |
| o-methylphenol | p-methylphenol |
| p-bromophenol | m-methylphenol |
| o-fluorophenol | p-methoxyphenol |

EXAMPLE XVIII

Methyl-2-(5-Carboxythiophen-2-yl)-9-oxo-15α-hydroxy-16-(m-trifluoromethylphenoxy)-5-cis-13-trans-α-tetranor-ω-tetranorprostadienoate To a solution of 80 mg. of 2-(5-carboxythiophen-2-yl)-9-oxo-15α-hydroxy-16-(m-trifluoromethylphenoxy)-5-cis-13-trans-α-tetranor-ω-tetranorprostadienoic acid in 10 ml. of ether is added a yellow solution of diazomethane in ether (prepared from N-methyl-N'-nitro-N-nitrosoguanidine) dropwise until the yellow color persists for 5 minutes. Concentration of the solution and silica gel chromatographic purification of the crude residue affords the title compound.

In a similar fashion, the compounds of Examples X, XII, XVI and XXI-XXIII may be converted into their methyl esters.

EXAMPLE XIX n-Decyl-2-(5-carboxythiophen-2-yl)-9-oxo-15α-hydroxy-16-(p-fluorophenoxy)-5-cis-13-trans-α-tetranor-ω-tetranorprostadienoate To a solution of 35 mg. of 2-(5-carboxythiophen-2-yl)-9-oxo-15α-hydroxy-16-(p-fluorophenoxy)-5-cis-13-trans-α-tetranor-ω-tetranorprostadienoic acid in 5 ml. of ether is added a yellow solution of diazodecane (prepared by oxidation of decyl hydrazine) dropwise until the yellow color persists for 5 minutes. Concentration of the solution and silica gel chromatographic purification of the crude residue affords the title compound.

In a similar fashion, the compounds of Examples X, XII, XVI and XXI-XXIII may be converted to their decyl esters. Following this same procedure, the other alkyl, cycloalkyl and phenylalkyl esters of the present invention may be prepared by treating the appropriate prostadienoic acid with the desired diazo compound which is prepared by oxidation of the corresponding hydrazine.

EXAMPLE XX

Cyclooctyl-2-(5-carboxythiophen-2-yl)-9α, 11α, 15α-trihydroxy-16-(β-naphthyloxy)-5-cis-13-trans-α-tetranor-ω-tetranorprostadienoate To a solution of 140 mg. of 2-(5-carboxythiophen-2-yl)-9α,11α, 15α-trihydroxy-16-(β-naphthyloxy)-5-cis-13-trans-α-tetranor-ω-tetranorprostadienoic acid in 7 ml. of dry methylene chloride is added 33 mg. (0.33 mmole) of triethyl amine. The mixture is stirred for 5 minutes then 36 mg. (0.33 mmole) of pivaloyl chloride is added. The solution is stirred for 45 minutes at room temperature under nitrogen then 192 mg. (1.5 mmole) of cyclooctyl alcohol and 225 μl of pyridine was added. The mixture is stirred at room temperature for an additional 2.0 hours then is diluted with ethyl acetate. The diluted solution is washed with water (2x) and saturated brine (1x), is dried (anhydrous magnesium sulfate), and is concentrated. Purification of the crude residue by silica gel chromatography provides the title compound.

In a similar fashion, the compounds of Examples X, XII, XVI, and XXI-XXIII may be converted to their cyclooctyl esters. Following this same procedure, the other alkyl, cycloalkyl and phenylalkyl esters of the present invention may be prepared by employing the appropriate alkanol.

EXAMPLE XXI

9α,11α,15α-trihydroxy-16-phenyloxy-ω-tetranor-α-tetranorprostanoic acid and
5-(2-carboxythiophen-5-yl)-9β,11α,15α-trihydroxy-16-phenyloxy-ω-tetranor-α-tetranorprostanoic acid.

To a solution of 100 mg of 5-(2-carboxythiophen-5-yl)9-oxo-11α,15α-dihydroxy-16-phenyloxy-ω-tetranor-α-tetranorprostanoic acid in 30 ml of methanol, cooled to 0°, is added a solution of 500 mg of sodium borohydride in 50 ml of methanol cooled to 0°. The reaction is let stir at 0° for 20 minutes for 1.0 hour at room temperature. The reaction is then diluted with 6 ml of water and is concentrated. The concentrated solution is overlaid with ethyl acetate then acidified to pH of 3 with 10% hydrochloric acid. The ethyl acetate layer is washed with water (2 × 10 ml) and saturated brine (10 ml), is dried (sodium sulfate) and is concentrated. The crude residue is purified by silica gel column chromatography to provide first 5-(2-carboxythiophen-5-yl)-11α,9α,15α-trihydroxy-16-phenyloxy-ω-tetranor-α-tetranorprostanoic acid, a mixture of C$_9$ epimers, and finally 9β,5-(2-carboxythiophen-5-yl)11α,15α-trihydroxy-16-phenyloxy-ω-tetranor-α-tetranorprostanoic acid.

The other compounds of Examples XII and XVII-XX may be reduced in a similar manner.

EXAMPLE XXII 5-(2-Carboxythiophen-5-yl)-9,15-dioxo-16-(m-tolyloxy(-5-cis-13-trans-ω-tetranor-α-tetranorprostadienoic acid To a solution, cooled to −10° under nitrogen, of 150 mg (0.35 mmole) 5-(2-carboxythiophen-5-yl)-9α,15α-dihydroxy-16-(m-tolyloxy)-5-cis, 13-trans-ω-tetranor-α-tetranorprostadienoic acid in 20 ml reagent grade acetone is added 0.28 ml. Jones' reagent. After 10 minutes at 0°, 5 drops of 2-propanol are added and the reaction mixture allowed to stir an additional 5 minutes at which time it is diluted with 50 ml ethyl acetate, washed with water (2 × 20 ml), brine (1 × 20 ml), dried (Na₂SO₄) and concentrated by rotary evaporation. The resultant crude oil is purified by column chromatography on silica gel (Brinkman). After elution of less polar impurities, the desired 5-(2-carboxythiophen-5-yl)-9,15-dioxo-16-(m-tolyloxy)-5-cis, 13-trans-ω-tetranor-α-tetranorprostadienoic acid is collected.

EXAMPLE XXIII 5-(2-Carboxythiophen-5-yl)-9α,11α-dihydroxy-15-oxo-16-phenoxy-5-cis-13-trans-ω-tetranor-α-tetranorprostadienoic acid A heterogeneous mixture of 70 mg of 5-(2-carboxythiophen-5-yl)-9α,11α,15α-trihydroxy-16-phenoxy-5-cis-13-trans-ω-tetranor-α-tetranorprostadienoic acid and 700 mg of activated manganese dioxide in 5 ml of methylene chloride is stirred at room temperature for 4 hours. The mixture is filtered, the filter cake washed with acetone, and the filtrate concentrated. Purification of the residue by silica gel chromatography provides the title compound.

In similar fashion, the 15-hydroxy compounds of Examples X and XII may be converted into the 15-keto PGE₂ and PGF₂α analogs of the present invention.

EXAMPLE XXIV

2-[5α-Hydroxy-2β-(3α-(tetrahydropyran-2-yloxy)-4-phenyloxybut-1-yl)-cyclopen-1α-yl]acetic acid, γ-lactone A heterogeneous mixture of 500 mg of 2-[5α-hydroxy-2β-(3α-(tetrahydropyran-2-yloxy)-4-phenyloxy-trans-buten-1-yl)cyclopent-1α-yl]acetic acid, and 50 mg of 5% rhodium on alumina in 5 ml of ethyl acetate is stirred under 1 atmosphere of hydrogen for 2 hours. The mixture then is filtered through a pad of Celite then is concentrated. Purification of the crude residue by silica gel chromatography affords the desired 2-[5α-hydroxy-2β-(3α-(tetrahydropyran-2-yloxy)-4-phenyloxybut-1-yl)cyclopent1α-yl]acetic acid, γ-lactone.

The product of this example may be converted into the 13,14-dihydroprostaglandin two-series analogs of this invention by the procedures of Examples VII, IX-XII and XVII-XXII.

What is claimed is:

1. An optically active compound of the structure

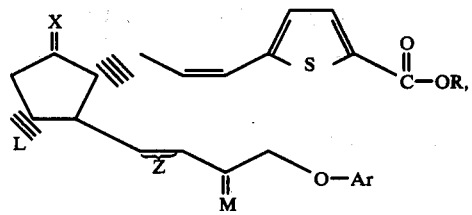

the optical antipode and the racemic mixture thereof wherein M and X are selected from the group consisting of

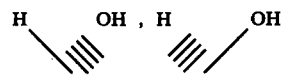

and keto;

Z is a trans double bond or single bond;

R is selected from the group consisting of hydrogen, alkyl of from one to ten carbon atoms, cycloalkyl of from three to eight carbon atoms, phenyl, phenylalkyl of from seven to nine carbon atoms and substituted phenyl wherein said substituent if fluoro, chloro, bromo, iodo, alkyl and alkoxy of from one to six carbon atoms, and phenyl;

L is selected from the group consisting of hydrogen and hydroxyl; and

Ar is selected from the group consisting of phenyl, α-naphthyl, β-naphthyl and monosubstituted phenyl wherein said substituent is selected from the group consisting of fluoro, chloro, bromo, trifluoromethyl, phenyl, and alkyl and alkoxy of from one to six carbon atoms.

2. A compound of claim 1 wherein Ar is phenyl.

3. A compound of claim 1 wherein X is keto and L is hydroxyl.

4. A compound of claim 1 wherein X is

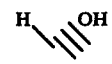

and L is hydroxyl.

5. A compound of claim 1 wherein M is

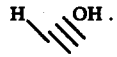

6. A compound of claim 1, 5-(2-carboxythiophen-5-yl)-9α,11α,15α-trihydroxy-16-phenoxy-cis-5-trans-13-ω-tetranor-α-tetranorprostadienoic acid.

7. A compound of claim 1, 5-(2-carboxythiophen-5-yl)-9-oxo-11α,15α-dihydroxy-16-phenoxy-cis-5-trans-13-ω-tetranor-α-tetranorprostadienoic acid.

* * * * *